United States Patent [19]

Locko et al.

[11] Patent Number: 4,703,070
[45] Date of Patent: Oct. 27, 1987

[54] SILICONE RUBBER CONTAINMENT OF ORGANIC LIQUIDS

[75] Inventors: George A. Locko, Trenton; Charles R. Frihart, Lawrenceville, both of N.J.

[73] Assignee: Union Camp Corporation, Wayne, N.J.

[21] Appl. No.: 886,986

[22] Filed: Jul. 16, 1986

[51] Int. Cl.$^4$ .................................................. A61L 9/01
[52] U.S. Cl. .................................... 523/102; 524/263; 524/264; 524/266; 524/262; 524/730; 524/731; 524/463; 428/905
[58] Field of Search ................ 523/102; 524/263, 264, 524/266, 730, 731, 463, 795, 262; 428/905; 252/522 A

[56] References Cited

U.S. PATENT DOCUMENTS 4,051,159  9/1977  Tsoucalas et al. ............... 252/522 A
4,419,484  12/1983  Sattlegger et al. .................. 524/731
4,524,018  6/1985  Yemoto et al. ..................... 428/905

FOREIGN PATENT DOCUMENTS 0126791   5/1983  European Pat. Off. ........ 252/522 A
57-040558  3/1982  Japan .
58-022063  2/1983  Japan ............................. 252/522 A
59-135240  8/1984  Japan ............................. 252/522 A

*Primary Examiner*—Lewis T. Jacobs
*Attorney, Agent, or Firm*—Kane, Dalsimer, Sullivan, Kurucz, Levy, Eisele and Richard

[57] ABSTRACT

Silicone rubber matrices are used to contain and dispense volatile, organic liquids. The articles, as dispensors are improved by the addition of a compatibilizing agent to reduce migration of the organic liquid out of the matrix in the form of liquid drops or films. Higher loadings of the organic liquid into the rubber matrix are achieved without syneresis occurring.

7 Claims, 2 Drawing Figures 4,703,070

SILICONE RUBBER CONTAINMENT OF ORGANIC LIQUIDS

BACKGROUND OF THE INVENTION

1. Field of the Invention

The invention relates to silicone rubber matrices for holding organic liquids such as fragrances for slow-release over a period of time to the atmosphere.

2. Brief Description of the Prior Art

Silicone rubber matrices for the containment and dispensing of volatile fragrances are well known in the art; see for example Japanese Patent Application No. 82-40,558. This reference describes a fragrant, rubber-like molding material, formed by dispersing a fragrance in a silicone rubber and then carrying out a cross-linking reaction with an organo-metal salt. The articles suffer from the disadvantage that migration of the fragrance out of the silicone rubber in the form of liquid drops occurs at even moderate loadings of volatile fragrance due to incompatibility of the silicone polymer and the volatile fragrance.

The present invention represents an advance in the art in that higher loadings of organic liquids for dispensing may be achieved, without syneresis, i.e.; without migration of the liquid to a surface of the silicone rubber matrix.

SUMMARY OF THE INVENTION

The invention comprises a device for the slow-release of a volatile, organic liquid to the atmosphere, which comprises;
a body of a silicone rubber matrix;
said matrix having dispersed therein the volatile, organic liquid, and an effective amount of a compatibilizing agent for compatibilization of the volatile, organic liquid with the silicone rubber.

The term "volatile, organic liquid" as used herein means a liquid organic compound, or mixture of liquid organic compounds, often polar in nature, which will evaporate into the atmosphere under ambient conditions of temperature and pressure.

The term "compatibilizing agent" is used throughout the specification and claims as meaning an organic compound which is chemically non-reactive with silicone rubber and the organic liquid to be dispersed in the rubber matrix, but which will reduce the natural tendency of the organic liquid to migrate out of the matrix and form liquid films or drops on the exposed surface of the rubber.

The devices of the invention are useful for the release of a volatile to the atmosphere over prolonged periods of time and find practical application as air fresheners, deodorizers, insect repellants, pheromone dispensors and the like.

The invention also comprises the method of manufacturing the devices of the invention.

DETAILED DESCRIPTION OF THE PREFERRED EMBODIMENTS OF THE INVENTION

Figure 1:
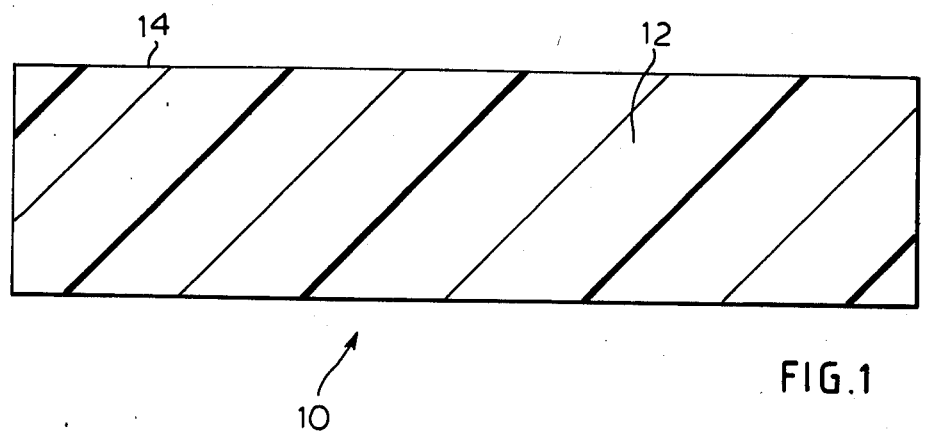
FIG. 1 is a cross-sectional side elevation of an embodiment device of the invention.

Silicone rubbers are well known compositions as are methods of their preparation. A wide variety are commercially available. In general, the silicone rubbers are prepared by curing a homogeneous mixture of silicone fluids or gums which may comprise fillers such as finely divided silica, diatomoceous earth, titanium dioxide, calcium carbonate, ferric oxide and the like; catalysts such as benzoyl peroxide, Bis(2,4-dichlorobenzoyl) peroxide, t-butyl peroxybenzoate, dicumyl peroxide, organometallic salts such as dibutyltin dilaurate, and the like; pigments, solvents and like additives. The rubber compositions may be cured (vulcanized) at room temperatures (RTV) or at elevated temperatures (HTV) depending on specific catalysts and/or cross-linking agents. Representative of cross-linking agents are alkyl silicates. Although any of the known silicone rubbers may be used as matrices in the present invention, the RTV compositions are preferred since they may be cured with the volatile organic liquid in-situ, without special precautions to prevent premature volatilization and loss of the liquid due to high temperature exposure.

One example of a silicone rubber which is advantageously used in the invention is Dow Corning 3110 RTV silicone rubber. This material can be cross-linked at room temperature with Dow Corning RTV catalyst No. 4. When allowed to cure in a suitable mold, this material will give a solid matrix body which can then be loaded with a liquid volatile and used as described herein.

The volatile organic liquid may be incorporated in the silicone rubber matrix by impregnation after curing of the rubber, but preferably the liquid is admixed with the RTV rubber components prior to curing to obtain a complete and homogeneous dispersion within the cured rubber matrix. In the latter case, the volatile organic liquid is simply admixed in the curable silicone rubber composition and the composition cured. Loadings of the volatile liquid into the cured rubber may be obtained, on a weight basis, within the range of from 5 to about 40; preferably 10 to 30 and most preferably above about 20%.

The volatile organic liquid may be any volatile or volatilizable substance which it is desired to release from the polymer into the surrounding atmosphere as a gas in order to perform a useful function. The invention is particularly applicable to fragrances, including natural, essential oils and synthetic perfumes, and blends thereof. Many fragrances are polar in nature because they contain substantial amounts of alcohols and other polar compounds. This invention is especially applicable to these polar fragrances. Typical perfumery materials which may form part of, or possibly the whole of, the gas for dispensing include: natural essential oils such as lemon oil, mandarin oil, clove leaf oil, petit-grain oil, cedar wood oil, patchouli oil, lavandin oil, neroli oil, ylang oil, rose absolute or jasmin absolute; natural resins such as labdanum resin or olibanum resin; single perfumery chemicals which may be isolated from natural sources or manufactured synthetically, as for example alcohols such as geraniol, nerol, citronellol, linalool, tetrahydrogeraniol, beta-phenylethyl alcohol, methyl phenyl carbinol, dimethyl benzyl carbonol, menthol or cedrol; acetates and other esters derived from such alcohols; aldehydes such as citral, citronellal, hydroxycitronellal, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; synthetic musks such as musk xylene, musk ketone and ethylene brassylate; and the like.

The compatibilizing agents employed in the invention are all well known compounds as are the methods of their preparation. More specifically, the agents are represented by 1. Low-to-medium molecular weight polysiloxanes of the general formula:

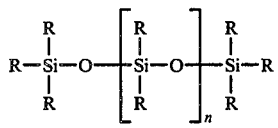

(I)

wherein n is an integer of at least 1 and such that the molecular weight (average) of the compound (I) does not exceed about 20,000; preferably less than about 5,000. Preferably R is an aliphatic or aromatic chain of 1 to 8 carbon atoms, most preferably alkyl such as methyl, ethyl, propyl, butyl, pentyl, heptyl, octyl and isomeric forms thereof or halogen-containing aliphatics or aromatic such as phenyl.

The polysiloxanes of the formula (I) given above include, for example, polydimethylsiloxanes (linear and branched), polymethylhexylsiloxane, polymethyloctylsiloxane, polymethyldodecylsiloxane and the like.

2. Derivatives of the polysiloxanes of the formula (I) given above, such as polysiloxane of the formula (I) described above, terminated by carbinol groups, e.g., groups of the formula:

(II)

or terminated by divinyl methyl groups, i.e.; of the formula:

(III)

or terminated by vinylphenylmethyl groups, i.e.; of the formula:

(IV)

3. Compounds that are fluorine-containing polar hydrocarbons with polar groups, for example, perfluorodecanol, perfluoroctanol, perfluorodecanoic acid and the like.

The compatibilizing agents may be loaded with the volatile, organic liquid into the silicone rubber in sufficient quantity to bring about a compatibilization between the liquid and the rubber. In general, the quantity required is within the range of from about 1 to about 10 percent by weight of the rubber.

Figure 2:
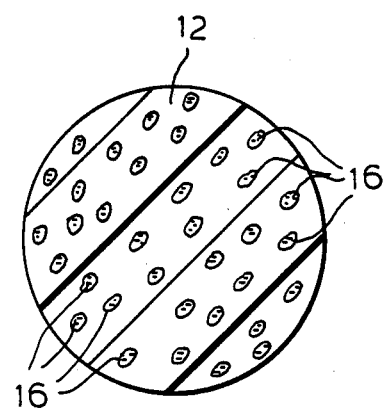
FIG. 2 is an enlarged view of a portion of the device of FIG. 1.

Referring now to the accompanying drawings, FIG. 1 is a cross-sectional side elevation of an embodiment device 10 of the invention made up of silicone rubber matrix 12 having surfaces 14 free of migrant volatile liquid. FIG. 2 is an enlarged view of a portion of the matrix 12 showing dispersed therein finely dispersed volatile, polar organic liquid 16. The liquid 16 is dispensed from the matrix 12 as a volatile over a prolonged period of time.

The following preparations and examples described the manner and process of making and using the invention and set forth the best mode contemplated by the inventors but are not to be construed as limiting. All parts are by weight unless otherwise indicated.

Preparation 1

A suitable aluminum pan was charged with proportions of Dow Corning Silastic HS RTV silicone rubber, a floral fragrance containing greater than 20% by weight of alcohols, a compatibilizer and Dow Corning Silastic HS catalyst. The contents of the pan were mixed vigorously.

EXAMPLE 1

Samples were prepared according to Preparation 1. The proportion of floral fragrance used in each sample was about 40% by weight. The compatibilizer used in each sample and the proportions of compatibilizer and Dow Corning Silastic HS catalyst used are given in Table 1. The extent to which the liquid fragrance could be blended into the mixture for each sample is given in Table 2.

TABLE 1

| Sample No. | Compatibilizer, Wt. % | Silastic HS Catalyst, Wt. % |
|---|---|---|
| 1-A | PS-555$^a$, 4.7 | 4.4 |
| 1-B | PS-556$^b$, 4.6 | 4.3 |
| 1-C | PS-071$^c$, 4.8 | 4.2 |
| 1-D | PS-037.5$^d$, 4.5 | 4.4 |
| 1-E | PS-441.2$^e$, 5.2 | 4.1 |
| 1-F | PS-537$^f$, 4.4 | 4.0 |
| 1-G | pentafluorodecanol-1, 4.7 | 4.2 |
| 1-H | Tween 60$^g$, 4.9 | 4.2 |
| 1-I | Brij 56$^h$, 4.8 | 4.4 |
| 1-J | Pentex 99$^i$, 4.8 | 4.6 |
| 1-K | Soybean Oil, 4.9 | 4.2 |

$^a$Petrarch Systems, Inc. product that is an ABA ethylenedimethylsiloxane oxide copolymer of 2400 molecular weight and contains 50% ethylene oxide.
$^b$Petrarch Systems, Inc. product that is an ABA ethylenedimethylsiloxane oxide copolymer of 1000-1500 molecular weight and contains 75-80% ethylene oxide.
$^c$Petrarch Systems, Inc. product that is a dimethylsiloxaneethylene oxide copolymer of 1200 molecular weight and contains 75% ethylene oxide.
$^d$Petrarch Systems, Inc. product that is a trimethylsiloxaneterminated polydimethylsiloxane of 550 molecular weight.
$^e$Petrarch Systems, Inc. product that is a vinyldimethylterminated polydimethylsiloxane of 200 centistoke viscosity.
$^f$Petrarch Systems, Inc. product that is a hydride-terminated polydimethylsiloxane of 400 molecular weight.
$^g$ICI Americas, Inc. product that is a polyoxyethylene (20) sorbitan monostearate.
$^h$ICI Americas, Inc. product that is polyoxyethylene (10) cetyl ether.
$^i$Colloids, Inc. product that is sodium dioctyl sulfosuccinate.

TABLE 2

| Sample No. | Compatibilizer | Relative Extent To Which Fragrance Is Blended Into Formulation |
|---|---|---|
| 1-A | PS-555 | Almost Complete |
| 1-B | PS-556 | Good |
| 1-C | PS-071 | Marginal |
| 1-D | PS-037.5 | Good |
| 1-E | PS-441.2 | Good |
| 1-F | PS-537 | Marginal |
| 1-G | pentafluorodecanol-1 | Marginal |
| 1-H | Tween 60 | Poor |
| 1-I | Brij 56 | Poor |
| 1-J | Pentex 99 | Poor |
| 1-K | Soybean Oil | Poor |

The Samples 1-H, 1-I, 1-J and 1-K are not samples of the invention but are made for comparative purposes.

Preparation 2

A suitable aluminum pan was charged with proportions of an RTV silicone rubber, a compatibilizer (no compatibilizer was added for control examples), a floral fragrance containing greater than 20% by weight of alcohols and a catalyst for curing the rubber. The contents of the pan were vigorously mixed, poured into plastic molds and securely enveloped in a polyvinylidene chloride (Saran ®) film. The enveloped compositions were allowed to cure at room temperature, removed from the molds, rewrapped in Saran ® film and then stored at room temperature for about 1-3 days. At the end of this period, the cured rubbers were removed from the film and observed for evidence of syneresis by a panel of nine people who graded the degree of liquid sweating or beading on the exposed surface of the cured rubber. Grading was on a scale of 0-10 (0=no sweating; 10=total wetness). The observed results were averaged and are given in Table 5 following Examples 2 and 3. The types and proportions of ingredients employed to prepare each article of the invention or a control, are given in the description of the example.

EXAMPLE 2

Samples were prepared according to Preparation 2. The proportions of floral fragrance, compatibilizer (PS-555, an ethoxylated polydimethylsiloxane) and Dow Corning RTV catalyst #4 (tin 2-ethylhexoate) used are given in Table 3. Dow Corning 3110 RTV silicone rubber was used to prepare all samples in Table 3.

TABLE 3

| Sample No. | Floral Fragrance, Wt. % | PS-555, Wt. % | RTV Catalyst #4, Wt. % |
|---|---|---|---|
| 2-A | 25.7 | 4.6 | 4.4 |
| 2-B | 20.0 | none | 7.5 |
| 2-C | 12.0 | none | 7.5 |
| 2-D | 20.0 | none | 1.4 |
| 2-E | 12.0 | none | 1.4 |

EXAMPLE 3

Samples were prepared according to Preparation 2. The proportions of floral fragrance, compatibilizer (PS-555) and Dow Corning Silastic HS catalyst used are given in Table 4. Dow Corning Silastic HS RTV silicone rubber was used to prepare all samples in Table 4.

TABLE 4

| Sample No. | Floral Fragrance, Wt. % | PS-555, Wt. % | Silastic HS Catalyst, Wt. % |
|---|---|---|---|
| 3-A | 29.8 | 5.0 | 4.2 |
| 3-B | 25.9 | 4.8 | 4.4 |
| 3-C | 20.0 | none | 7.5 |
| 3-D | 20.0 | none | 4.1 |
| 3-E | 12.0 | none | 7.5 |

TABLE 5

| Example and Sample No. | Floral Fragrance Wt. % | Type Silicone Rubber Used | PS-555 Wt. % | Rating by Panel (Average) |
|---|---|---|---|---|
| 2-A | 25.7 | Dow Corning 3110 | 4.6 | 4.8 |
| 2-B | 20.0 | Dow Corning 3110 | none | 6.2 |
| 2-C | 12.0 | Dow Corning 3110 | none | 7.2 |
| 2-D | 20.0 | Dow Corning 3110 | none | 8.2 |
| 2-E | 12.0 | Dow Corning 3110 | none | 8.4 |
| 3-A | 29.8 | Silastic HS | 5.0 | 3.0 |
| 3-B | 25.9 | Silastic HS | 4.8 | 2.2 |

TABLE 5-continued

| Example and Sample No. | Floral Fragrance Wt. % | Type Silicone Rubber Used | PS-555 Wt. % | Rating by Panel (Average) |
|---|---|---|---|---|
| 3-C | 20.0 | Silastic HS | none | 1.2 |
| 3-D | 20.0 | Silastic HS | none | 1.8 |
| 3-E | 12.0 | Silastic HS | none | 4.2 |

The samples 2-B, 2-C, 2-D, 2-E, 3-C, 3-D and 3-E are not examples of the invention but are made for comparative purposes.

What is claimed is:

1. A device for the slow-release of a volatile, organic liquid to the atmosphere, which comprises;
   a body of a silicone rubber matrix;
   said matrix having dispersed therein the volatile, organic liquid, and an effective amount of a compatibilizing agent for compatibilization of the volatile, organic liquid with the silicone rubber, said agent comprising a member selected from the group consisting of
   (A) polysiloxanes of the general formula:

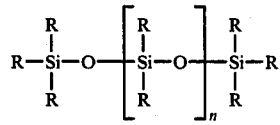

wherein n is an integer of at least 1 and such that the molecular weight (average) of the agent does not exceed about 20,000; R is selected from an aliphatic or aromatic chain of 1 to 8 carbon atoms;
   (B) a compound selected from ethylene-dimethylsiloxane oxide ABA block copolymers wherein the B segment is represented by the general formula given above, (C) derivatives of the polysiloxanes (A); which are terminated by groups selected from carbinol groups of the formula:

$-CH_2-CH_2-OH$ divinyl methyl groups of the formula:

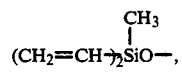

or vinylphenylmethyl groups of the formula:

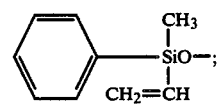

(D) compounds that are fluorine-containing polar hydrocarbons with polar groups.

2. The device of claim 1 wherein the silicone rubber is a room temperature vulcanized rubber.

3. The device of claim 1 wherein the organic liquid is a fragrance.

4. The device of claim 1 wherein the effective amount is a proportion within the weight range of from 1 to 10 parts by weight of the device.

5. The device of claim 1 wherein the agent is selected from the group consisting of the low molecular weight polysiloxanes (A) and polysiloxane derivatives (C) containing vinyl, hydrogen, phenyl or carbinol groups.

6. The device of claim 1 wherein the agent is selected from the group consisting of fluorine-containing hydrocarbons with polar groups.

7. The device of claim 1 wherein the agent is an ABA ethylenedimethylsiloxane oxide copolymer.

* * * * *